(12) United States Patent
Haidukewych

(10) Patent No.: US 8,556,986 B2
(45) Date of Patent: Oct. 15, 2013

(54) ACETABULAR PROSTHETIC DEVICE

(76) Inventor: George J. Haidukewych, Orlando, FL (US)

( * ) Notice: Subject to any disclaimer, the term of this patent is extended or adjusted under 35 U.S.C. 154(b) by 30 days.

(21) Appl. No.: 13/374,841

(22) Filed: Jan. 18, 2012

(65) Prior Publication Data

US 2013/0184832 A1 Jul. 18, 2013

(51) Int. Cl.
*A61F 2/32* (2006.01)
(52) U.S. Cl.
USPC ............... 623/22.38; 623/22.11; 623/22.21
(58) Field of Classification Search
CPC ........................................................ A61F 2/34
USPC ................. 623/22.11, 22.15–22.39
See application file for complete search history.

(56) References Cited

U.S. PATENT DOCUMENTS

2005/0171614 A1* 8/2005 Bacon .................. 623/22.19
2013/0035766 A1* 2/2013 Meridew ............... 623/22.21

* cited by examiner

*Primary Examiner* — Thomas Sweet
*Assistant Examiner* — Jason-Dennis Stewart
(74) *Attorney, Agent, or Firm* — Arthur W. Fisher, III

(57) ABSTRACT

An acetabular prosthetic device comprising at least one acetabular augment coupled to an acetabular cup by an augment coupling element to secure the acetabular prosthetic device in place wherein the acetabular cup comprises a shell having at least one groove formed on the outer surface thereof to slidably receive the augment coupling element therein and the acetabular augment comprises an augment body configured to engage the shell and the ilia bone such that the augment coupling element is moved along the groove to position the acetabular body to engage both the shell and ilia bone to secure the acetabular prosthetic device in place.

14 Claims, 5 Drawing Sheets

ACETABULAR PROSTHETIC DEVICE

BACKGROUND OF THE INVENTION

1. Field of the Invention

An acetabular prosthetic device for use with a prosthetic hip implant comprising at least one acetabular augment coupled to an acetabular cup to secure the acetabular prosthetic device in place.

2. Description of the Prior Art

U.S. Pat. No. 5,176,711 shows an implantable acetabular hip prosthesis including a primary shell having an outer surface to be received within a surgically prepared acetabulum and an inner cavity for receiving a bearing insert which, in turn, receives a femoral head portion of a femoral component of a total hip prosthesis. The acetabular component of the prosthesis further includes an augmentation piece to be attached to the primary shell fixedly retained in a selected one of a plurality of angular orientations relative to the primary shell.

U.S. Pat. No. 6,454,809 describes a acetabular or cotyloid implant having at least one dove-tail groove found on an outer surface thereof to receive an augmentation element.

U.S. Pat. No. 7,985,260 and US 2011/0264232 show an acetabular prosthesis system coupled to a surgically-prepared acetabulum includes an acetabular shell, an augment component and a fastener to couple the acetabular shell and the augment component together.

U.S. Pat. No. 7,993,408 teaches an orthopedic prosthesis for implantation comprising a shell, an augment and a securing member. An elongated slot extends between the outer and inner surfaces of the shell. The augment defines a body having a passage therethrough. The securing member extends through the passage and the slot. The securing member is movable between a locked position wherein the augment is precluded from relative movement with the shell and an unlocked position wherein the securing member is adapted to slidably traverse along the slot to locate the augment at a plurality of positions relative to the shell.

US 2008/0021568 relates to a prosthetic acetabular cup having an augment attached to an acetabular cup by a coupling element including an outer dovetail portion which slidably engages a groove formed within the augment. The inner end of the coupling element engages screw holes on the acetabular cup. The groove of the augment further includes a second end having a gradually increasing distance from the outer surface of the shell and the inner surface of the augment on moving towards the second end of the augment.

Additional examples are found in the following prior art: U.S. Pat. No. 7,595,715, U.S. Pat. No. 7,947,083, US 2007/0173948 and US 2010/00044754

While some of the prior art may contain some similarities relating to the present invention, none of them teach, suggest or include all of the advantages and unique features of the invention disclosed hereafter.

SUMMARY OF THE INVENTION

The present invention relates to an acetabular prosthetic device for use with a prosthetic hip implant comprising at least one acetabular augment coupled to an acetabular cup by an augment coupling element to secure the acetabular prosthetic device to the ilia bone.

The acetabular cup comprises a shell to rotatably receive a substantially spherical portion of the prosthetic hip implant therein having at least one groove formed therein to slidably receive the augment coupling element.

The acetabular augment comprises an augment body to engage the outer surface of the shell having at least one coupling aperture to receive a corresponding fastener or screw therethrough, to operatively engage the augment coupling element to secure the acetabular augment to the acetabular cup when the acetabular prosthetic device is surgically positioned in the patient and a bone engaging surface to engage the ilia bone having at least one acetabular aperture to receive a corresponding fastener or screw therethrough to secure the augment body to the ilia bone when the acetabular augment and the acetabular cup are surgically positioned in the patient.

The augment coupling element comprises an enlarged inner member and an internally threaded reduced outer member. The groove formed in the shell comprises a conversely shaped configuration to the augment coupling element, i.e., an enlarged inner or interior space configured to receive the enlarged inner member of the augment coupling element and a reduced outer slot to receive the internally threaded reduced outer member of the acetabular coupling element such that when a fastener or screw is passed through the augment body of the acetabular augment and threaded into the internally threaded reduced outer member the surface of the enlarged inner member and the surface of the distal enlarged space are pressed together to secure the acetabular augment in place along the groove.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

Similar reference characters refer to similar parts throughout the several views of the drawings.

DETAILED DESCRIPTION OF THE INVENTION

Figure 1:
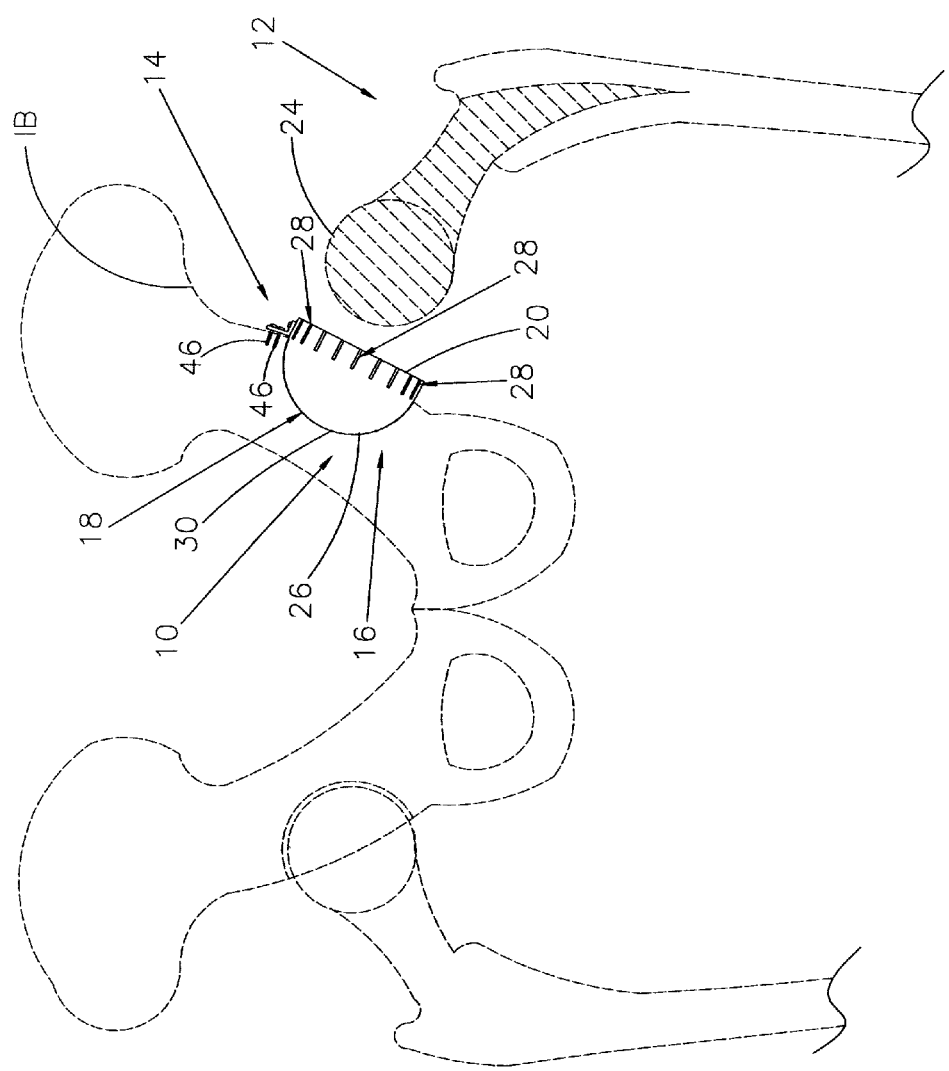
FIG. 1 is a side view of the acetabular prosthetic device of the present invention.
Figure 2:
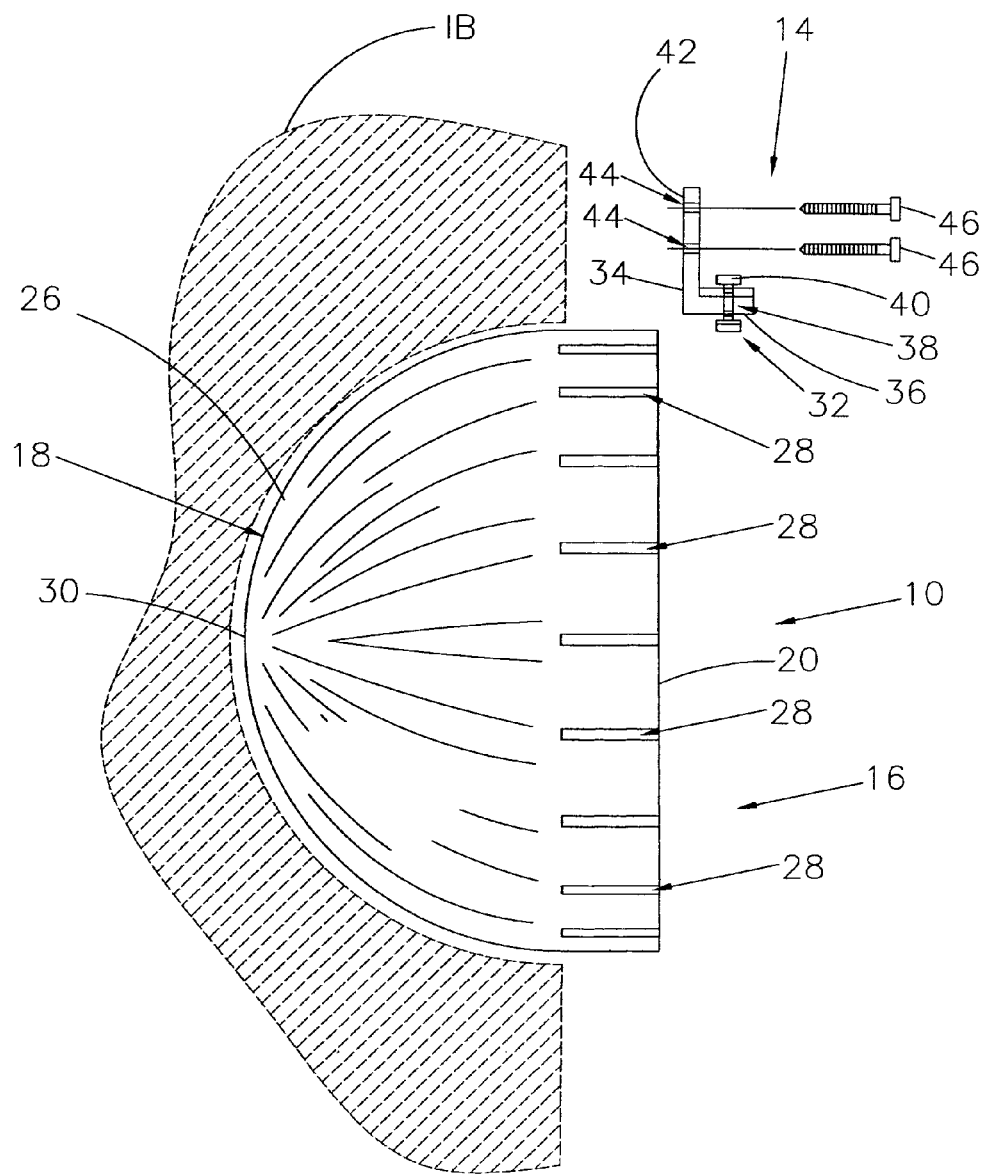
FIG. 2 is an exploded side view of the acetabular prosthetic device of the present invention.
Figure 3:
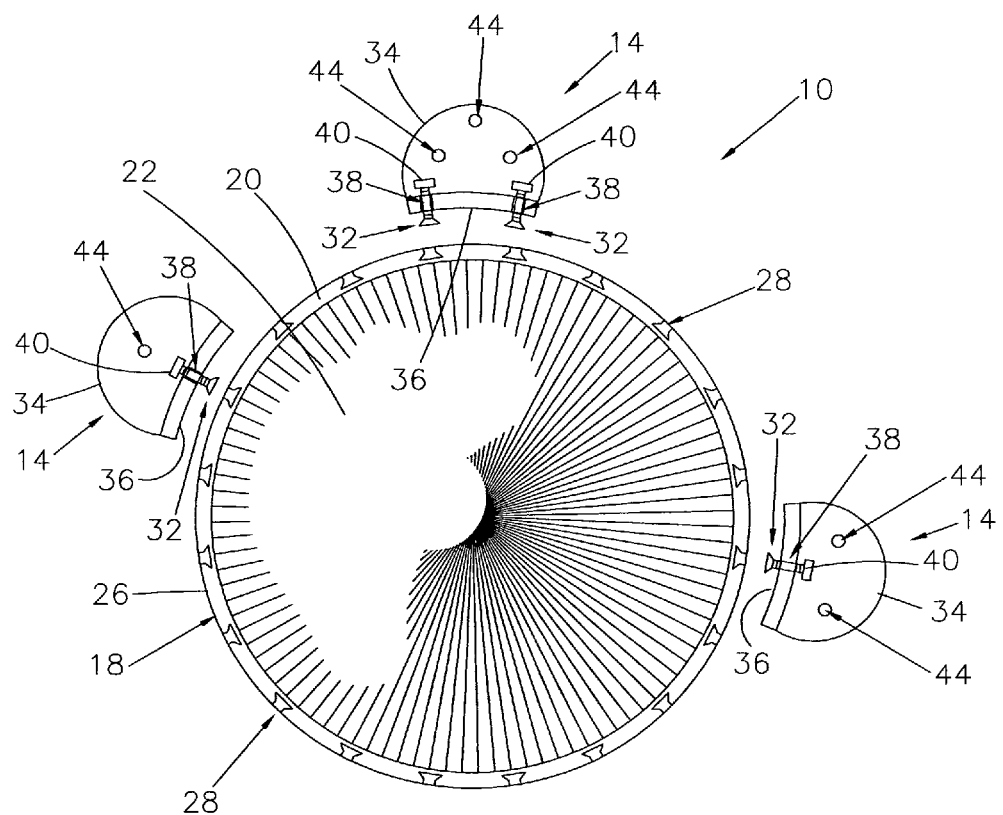
FIG. 3 is an exploded bottom view of the acetabular prosthetic device of the present invention.
Figure 4:
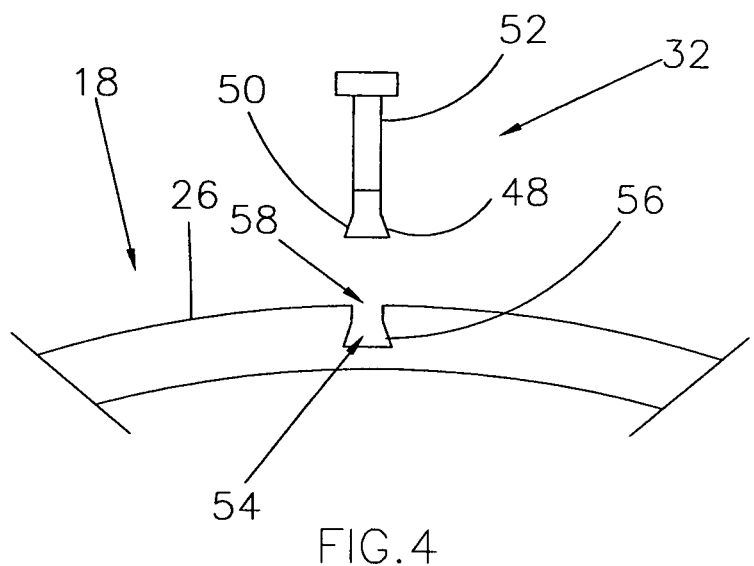
FIG. 4 is a side view of the augment coupling element of the present invention.
Figure 5:
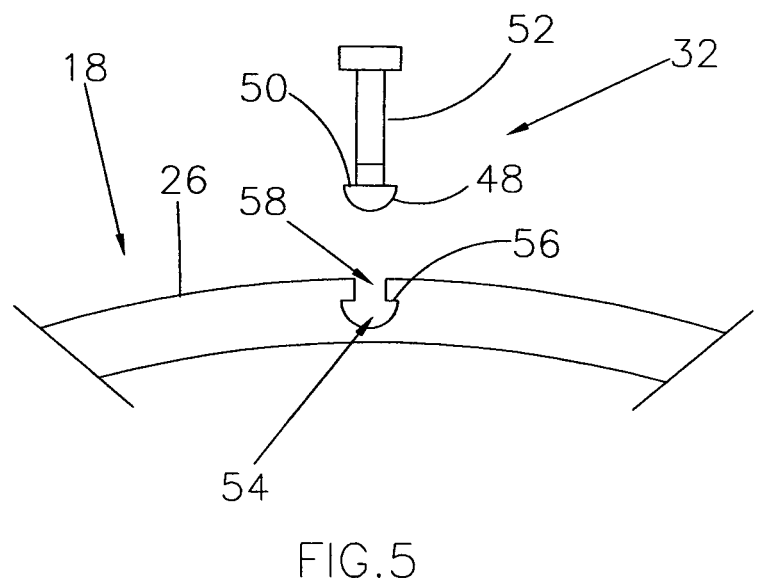
FIG. 5 is a side view of an alternate embodiment of the augment coupling element of the present invention.
Figure 6:
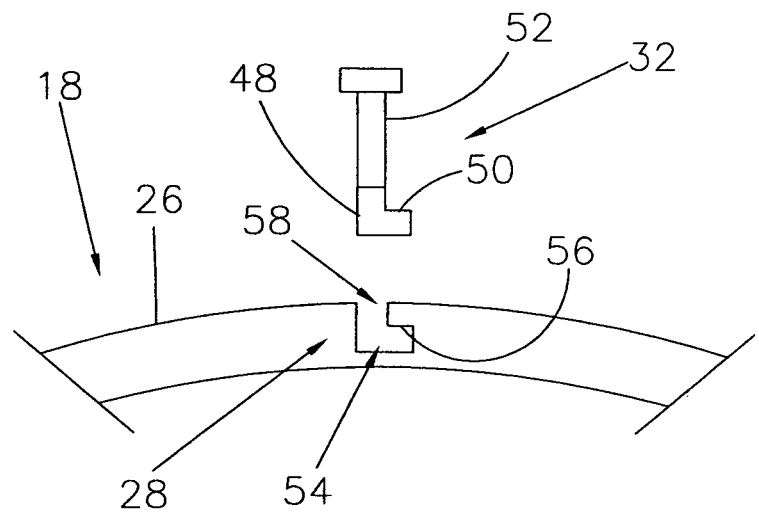
FIG. 6 is a side view of another alternate embodiment of the augment coupling element of the present invention.
Figure 7:
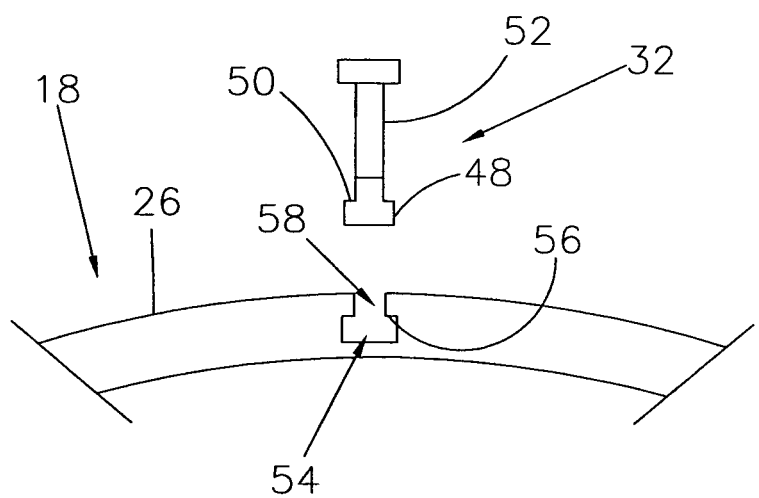
FIG. 7 is a side view of yet another alternate embodiment of the augment coupling element of the present invention.

As shown in FIGS. 1 through 3, the present invention relates to an acetabular prosthetic device generally indicated as 10 for use with a prosthetic hip implant generally indicated as 12 comprising at least one acetabular augment generally indicated as 14 coupled to an acetabular cup generally indicated as 16 to secure the acetabular prosthetic device 10 in place on the ilia bone (IB).

The acetabular cup 16 comprises a shell generally indicated as 18 including a substantially circular base 20 having an inner substantially concave surface 22 to rotatably receive a substantially spherical portion 24 of the prosthetic hip implant 12 therein and an outer substantially convex surface 26 having at least one groove 28 formed therein extending from the substantially circular base 20 of the shell 18 of the acetabular cup 16 toward the apex 30 thereof to slidably receive an augment coupling element generally indicated as 32.

The acetabular augment 14 comprises an augment body 34 including a substantially concave surface 36 to engage the outer substantially convex surface 26 of the shell 18 of the acetabular cup 16 having at least one coupling aperture or recess 38 to receive a corresponding fastener or screw 40 therethrough to operatively engage the augment coupling element 32 to secure the augment body 34 of the acetabular augment 14 to the shell 18 of the acetabular cup 16 when the acetabular prosthetic device 10 is surgically positioned in the patient and a bone engaging surface 42 to engage the ilia bone IB having at least one acetabular aperture or recess 44 to receive a corresponding fastener or screw 46 therethrough to secure the augment body 34 of the acetabular augment 14 to the ilia bone IB when the acetabular augment 14 and the acetabular cup 16 are surgically positioned in the patient. As best shown in FIG. 2, the center-line(s) of fastener(s) or screw(s) 40 is substantially perpendicular to the center-line(s) of fastener(s) or screw(s) 46.

FIGS. 4 through 7 show several embodiments of the augment coupling element 32. Specifically, each augment coupling element 32 comprises a distal enlarged inner member 48 including a proximal surface 50 and a proximal internally threaded reduced outer member 52 to receive the corresponding fastener or screw 40. The groove 28 formed in the shell 18 of the acetabular cup 18 comprises a converse configuration to the corresponding augment coupling element 32, i.e., a distal enlarged inner or interior space 54 including a proximal surface 56 configured to receive the correspondingly shaped distal enlarged inner member 48 of the augment coupling element 32 such that the proximal surface 50 of the distal enlarged inner member 48 engages the proximal surface 56 of the distal enlarged inner or interior space 54 and a reduced outer slot 58 to receive the proximal internally threaded reduced outer member 52 of the corresponding acetabular coupling element 32. When a fastener(s) or screw(s) 40 is passed through the coupling aperture(s) or recess(es) 38 formed in the augment body 34 of the acetabular augment 14 and threaded into the proximal internally threaded reduced outer member 52, the proximal surface 50 of the distal enlarged inner member 48 and the proximal surface 56 of the distal enlarged inner or interior space 54 are pressed together to secure the acetabular augment 14 in place operatively positioned along the groove 28 with the bone engaging surface 48 secured to the ilia bone IB by a fastener(s) or screw(s).

In particular, FIGS. 4 through 7 depict the distal enlarged inner end portion 48 as a frustum conical or truncated triangular in cross-section configuration, a hemispherical configuration, an L-shaped configuration and a T-shaped configuration respectively with the corresponding groove 28 having a converse configuration, in addition to the acetabular cup 16.

Of course, the shell 18 of the acetabular cup 16 may be glued or otherwise fastened or secured in typical fashion, surgical procedure.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An acetabular prosthetic device for use with a prosthetic hip implant comprising an acetabular cup coupled to at least one acetabular augment by a corresponding augment coupling element to anchor said acetabular prosthetic device to the ilia bone:

said acetabular cup comprises a shell having an apex and including a substantially concave inner surface to rotatably receive a substantially spherical portion of the prosthetic hip implant therein and a substantially convex outer surface having at least one groove including an enlarged inner portion and a reduced outer portion formed therein to receive at least a portion of said augment coupling element;

said acetabular augment comprises an augment body including a substantially concave shell engaging surface having a coupling aperture formed therethrough and configured to engage said substantially convex outer surface of said shell and a bone engaging surface having a acetabular aperture formed therethrough and configured to engage the ilia bone;

said augment coupling element comprises an enlarged distal inner member disposed within said enlarged inner portion of said groove to retain said enlarged distal inner member therein and said reduced proximal member at least partially disposed within said reduced outer portion of said groove and extending outwardly from said reduced outer portion of said groove;

said augment coupling element longitudinally movable within said groove to slidably move said bone engaging surface into engagement within the ilia bone;

said acetabular prosthetic device further including an anchor fastener extending through said acetabular aperture to anchor said bone engaging surface of said acetabular augment to the ilia bone; and when said augment coupling element is moved toward said apex until said bone engaging surface engages the ilia bone; and said augment coupling element further including a securing fastener to engage said reduced proximal member to secure said substantially concave surface of said acetabular augment to said substantially convex outer surface of said shell of said acetabular cup when said augment coupling element is operatively positioned along said groove when said bone engaging surface anchored to the ilia bone.

2. The acetabular prosthetic device of claim 1 wherein said groove formed in said substantially convex outer surface shell of said acetabular cup comprises an enlarged inner portion of a converse configuration to said enlarged distal inner member of said augment coupling member to receive said distal enlarged shaped inner member of said augment coupling element such that said enlarged distal inner member engages said enlarged inner portion to secure said substantially concave shell engaging surface to said substantially convex surface of said shell when said securing fastener engages said reduced proximal member of said augment coupling element.

3. The acetabular prosthetic device of claim 2 wherein said distal enlarged inner end portion is a frustum conical configuration with the corresponding groove having a converse configuration.

4. The acetabular prosthetic device of claim 2 wherein said distal enlarged inner end portion is a hemispherical configuration with the corresponding groove having a converse configuration.

5. The acetabular prosthetic device of claim 2 wherein said distal enlarged inner end portion is an L-shaped configuration with the corresponding groove having a converse configuration.

6. The acetabular prosthetic device of claim 2 wherein said distal enlarged inner end portion is a T-shaped configuration with the corresponding groove having a converse configuration.

7. The acetabular prosthetic device of claim 2 wherein said distal enlarged inner end portion is truncated triangular in cross-section configuration with the corresponding groove having a converse configuration.

8. An acetabular prosthetic device for use with a prosthetic hip implant comprising acetabular cup coupled to at least one acetabular augment by a corresponding augment coupling element to anchor said acetabular prosthetic device to the ilia bone:
   said acetabular cup comprises a shell having an apex including a substantially concave inner surface to rotatably receive a substantially spherical portion of the prosthetic hip implant therein and a substantially convex outer surface having at least one groove including an enlarged inner portion and a reduced outer portion formed therein to receive at least a portion of said augment coupling element;
   said acetabular augment comprises an augment body including a substantially concave shell engaging surface configured to engage said substantially convex outer surface of said shell and a bone engaging surface configured to engage the ilia bone;
   said augment coupling element comprises an enlarged distal inner member disposed within said enlarged inner portion of said groove to retain said enlarged distal inner member therein and said reduced proximal member at least partially disposed within said reduced outer portion of said groove extending outwardly from said groove;
   said augment coupling element longitudinally movable within said groove to move said bone enlarging surface into engagement within the ilia bone;
   such that said augment coupling element is operatively positioned on said acetabular cup wherein said bone engaging surface of said augment body is anchored to the ilia bone and said substantially concave shell engaging surface of said augment body is secured to said substantially convex outer surface of said shell of said acetabular cup.

9. The acetabular prosthetic device of claim 8 wherein said groove formed in said substantially convex outer surface shell of said acetabular cup comprises an enlarged inner portion of a converse configuration to said enlarged distal inner member of said augment coupling member to receive said distal enlarged shaped inner member of said augment coupling element to secure said substantially concave shell engaging surface to said substantially convex surface of said shell.

10. The acetabular prosthetic device of claim 9 wherein said distal enlarged inner end portion is a frustum conical configuration with the corresponding groove having a converse configuration.

11. The acetabular prosthetic device of claim 9 wherein said distal enlarged inner end portion is a hemispherical configuration with the corresponding groove having a converse configuration.

12. The acetabular prosthetic device of claim 8 wherein said distal enlarged inner end portion is an L-shaped configuration with the corresponding groove having a converse configuration.

13. The acetabular prosthetic device of claim 8 wherein said distal enlarged inner end portion is a T-shaped configuration with the corresponding groove having a converse configuration.

14. The acetabular prosthetic device of claim 8 wherein said distal enlarged inner end portion is truncated triangular in cross-section configuration with the corresponding groove having a converse configuration.

* * * * *